United States Patent
Fare et al.

(10) Patent No.: US 8,979,770 B2
(45) Date of Patent: Mar. 17, 2015

(54) EXTRACTION AND DIAGNOSTIC FLUID DEVICES, SYSTEMS AND METHODS OF USE

(75) Inventors: Thomas L. Fare, Sammamish, WA (US); Deborah A. Kessler, Bellevue, WA (US); Kristopher A. Kilian, Chicago, IL (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1573 days.

(21) Appl. No.: 12/280,504

(22) PCT Filed: Feb. 15, 2007

(86) PCT No.: PCT/US2007/062244
§ 371 (c)(1),
(2), (4) Date: Oct. 24, 2008

(87) PCT Pub. No.: WO2007/100986
PCT Pub. Date: Sep. 7, 2007

(65) Prior Publication Data
US 2009/0280470 A1 Nov. 12, 2009

Related U.S. Application Data

(60) Provisional application No. 60/776,257, filed on Feb. 24, 2006.

(51) Int. Cl.
*B65D 81/00* (2006.01)
*A61B 5/00* (2006.01)
*A01N 1/02* (2006.01)
*C12N 15/10* (2006.01)

(52) U.S. Cl.
CPC .................................. *C12N 15/1017* (2013.01)
USPC .............................. 600/584; 600/573; 435/2

(58) Field of Classification Search
CPC ............. A61M 2202/0413; A61M 2202/0439; A61M 2202/005; A61M 1/3633
USPC ....................................... 600/573–584; 435/2
See application file for complete search history.

(56) References Cited

U.S. PATENT DOCUMENTS

| | | |
|---|---|---|
| 4,880,548 A | 11/1989 | Pall |
| 4,923,620 A | 5/1990 | Pall |
| 4,925,572 A | 5/1990 | Pall |
| 5,100,564 A | 3/1992 | Pall |
| 5,229,012 A | 7/1993 | Pall |

(Continued)

OTHER PUBLICATIONS

Belgrader, P., et al., "Rapid and Automated Cartridge-Based Extraction of Leukocytes From Whole Blood for Microsatellite DNA Analysis by Capillary Electrophoresis," Clinical Chemistry 47(10):1929-1931, Oct. 2001.

(Continued)

*Primary Examiner* — Adam Eiseman
(74) *Attorney, Agent, or Firm* — Christensen O'Connor Johnson Kindness PLLC

(57) ABSTRACT

The present invention provides devices, systems and methods for RNA isolation from biological samples containing white blood cells, such as whole blood. The devices have a device body that includes a first chamber having a first membrane that selectively binds white blood cells, a second chamber having a second membrane that reversibly binds RNA and a plurality of ports that are removably attached to a reagent pack and waste receptacle via a valving system controlled by a control unit.

39 Claims, 8 Drawing Sheets

(56) References Cited

U.S. PATENT DOCUMENTS

| | | |
|---|---|---|
| 5,344,561 A | 9/1994 | Pall |
| 5,501,795 A | 3/1996 | Pall |
| 6,132,997 A | 10/2000 | Shannon |
| 6,136,555 A | 10/2000 | Jones |
| 6,218,531 B1 | 4/2001 | Ekenberg |
| 6,692,918 B2 | 2/2004 | Kurn |
| 6,749,748 B1 | 6/2004 | Macpherson |
| 6,946,251 B2 | 9/2005 | Kurn |
| 7,071,380 B1 * | 7/2006 | Lough et al. .............. 800/290 |
| 7,416,892 B2 | 8/2008 | Battrell |
| 2001/0016312 A1 * | 8/2001 | Lader .............................. 435/2 |
| 2003/0134417 A1 | 7/2003 | Brandwein |
| 2004/0005614 A1 | 1/2004 | Kurn |
| 2004/0157220 A1 | 8/2004 | Kurnool |
| 2004/0265864 A1 | 12/2004 | Mitsuhashi |
| 2005/0208501 A1 | 9/2005 | Goldrick |

OTHER PUBLICATIONS

Bibikova, M., et al., "Gene Expression in Formalin-Fixed, Paraffin-Embedded Tissues Obtained With a Novel Assay for Microarray Analysis," Clinical Chemistry 50(12):2384-2386, Dec. 2004.

Haskill, S., et al., "Adherence Induces Selective mRNA Expression of Monocyte Mediators and Proto-Oncogenes," Journal of Immunology 140(5):1690-1694, Mar. 1988.

Oroskar, A.A., "Development Applications for Membrane-Bottom Microwell Plates," IVD Technology Magazine, Jan. 1998, <http://www.devicelink.com/ivdt/archive/98/01/011.html> [retrieved Nov. 6, 2009], 11 pages.

Pahl, A., and K. Brune, "Stabilization of Gene Expression Profiles in Blood After Phlebotomy," Clinical Chemistry 48(12):2251-2253, Dec. 2002.

Rainen, L., et al., "Stabilization of mRNA Expression in Whole Blood Samples," Clinical Chemistry 48(11):1883-1890, Nov. 2002.

Shalon, D., et al., "A DNA Microarray System for Analyzing Complex DNA Samples Using Two-Color Fluorescent Probe Hybridization," Genome Research 6(7):639-645, Jul. 1996.

Simpkins, S.A., et al., "An RNA Transcription-Based Amplification Technique (NASBA) for the Detection of Viable *Salmonella enterica*," Letters in Applied Microbiology 30(1):75-79, Jan. 2000.

Urdea, M.S., et al., "Branched DNA Amplification Multimers for the Sensitive, Direct Detection of Human Hepatitis Viruses," Nucleic Acids Symposium Series (24):197-200, Feb. 1991.

Wang, X., and B. Seed, "A PCR Primer Bank for Quantitative Gene Expression Analysis," Nucleic Acids Research 31(24):e154(1-8) Dec. 2003.

"Filter Media, Leukosorb®," Pall Corporation, Ann Arbor, Mich., on Component Database, Jan. 1, 2006, <http://www.medibix.com/runsearch.jp?view=sku&product_id=454637> [retrieved Jan. 6, 2006], 2 pages.

"Glass Fiber Filter: Glass Fiber Filter Without Binder, 8×10 in.," © 2006 Millipore Corporation, Billerica, Mass., <http://www.millipore.com/catalogue.nsf/docs/AP408X105> [retrieved Jan. 6, 2006], 2 pages.

"Glass Fiber Filters," Pall Corporation, Ann Arbor, Mich., <http://www.labfilters.com/catalog/924_20027.asp> [retrieved Jan. 6, 2006], 4 pages.

"TCLP Glass Fiber Filters," Pall Corporation, Ann Arbor, Mich., <http://www.labfilters.com/catalog/924_20071.asp> [retrieved Jan. 6, 2006], 3 pages.

* cited by examiner

EXTRACTION AND DIAGNOSTIC FLUID DEVICES, SYSTEMS AND METHODS OF USE

FIELD OF THE INVENTION

The present invention relates to devices, systems and methods for RNA isolation from biological samples containing white blood cells, such as whole blood.

BACKGROUND OF THE INVENTION

Circulating leukocytes in whole blood have the potential to be used as indicators of infection, cancer, inflammation, and genetic and metabolic disease. For example, expression profiling assays have been used to identify changes in mRNA patterns that are associated with inflammation and metastatic disease and exposure to toxic and infectious agents. However, the purification of nucleic acid material from whole blood for diagnostic assays has been difficult for several reasons including the low concentration of actively metabolizing cells (only about 0.1 to 0.2% leukocytes), the high concentration of intracellular and extracellular ribonucleases, and the presence of high numbers of immature red blood cell reticulocytes which contain high levels of mRNA for $\alpha$ and $\beta$ globin. Hemoglobin mRNA associated with immature red blood cells can lead to cross hybridization and a subsequent decrease in sensitivity and specificity during microarray experiments.

Analysis of RNA isolated from whole blood for expression patterns indicative of disease requires that the isolated RNA and (optionally) amplified RNA accurately represent the status of WBC in the whole blood sample. In this regard, transcriptional inactivation is important to achieve at the time of blood sample collection in order to obtain nucleic acid material that is intact and accurately reflects the state of the subject. It is known that mRNA is unstable in untreated whole blood samples over time. For example, adherence of monocytes to the plastic walls of tubes used for blood collection has been shown to induce mRNAs for proinflammatory cytokines (see Haskill et al., *J. Immunol.* 140:1690-1694 (1988)). Lag times of greater than one hour between sample collection and processing have been reported to cause alterations in several cytokine mRNAs in human whole blood (Pahl et al., *Clinical Chem.* 48: 2251-2253 (2002)). A recent study by Rainen et al. demonstrated an increase in some mRNA levels (e.g., interleukin 8, c-jun) and a decrease in other mRNA levels (e.g., caspase 1, heat shock protein 70) over time (4 hours, 8 hours, 3 days and 5 days) in a panel of 25 mRNAs analyzed from samples of untreated whole blood isolated from a single donor (Rainen et al., *Clinical Chem.* 48:1883-1890 (2002)).

Current methods for nucleic acid purification from whole blood (i.e., erythrocyte lysis and Ficoll gradient separation, etc.) are time consuming, labor intensive, and not amenable to high throughput applications. Techniques that are amenable to high throughput applications such as reverse transcription, amplification, sequencing, and microarray hybridization, require nucleic acid material that is substantially free of contaminants capable of interfering with such processing or analytical procedures. Such contaminants include substances that block or inhibit chemical reactions (e.g., nucleic acid or protein hybridizations, enzymatically catalyzed reactions, and other types of reactions used in molecular biological techniques), and substances that catalyze the degradation or de-polymerization of a nucleic acid. Contaminants also include macromolecular substances from the sample from which a nucleic acid material of interest is isolated, including enzymes, other types of proteins, red blood cells, polysaccharides, and lipids. Contaminants may also be introduced into a target nucleic acid sample from chemicals or other materials used to isolate the nucleic acid material from other substances, such as trace metals and organic solvents. Specifically with respect to the isolation of RNA from whole blood, it is important that the isolated RNA be substantially free from contamination with heme, a well known inhibitor of reverse transcription and DNA polymerase, as well as globin message, which can interfere with hybridization-based assays.

Therefore, there is a need in diagnostic molecular profiling and biomarker discovery for methods and devices that rapidly purify nucleic acid material from whole blood. In particular there is a need for methods and devices for isolating RNA from a sample of whole blood, whereby the RNA is substantially free of contaminants, including proteins, lipids, genomic DNA, globin message, and any chemicals likely to inhibit or interfere with processing or analysis of the isolated RNA, such that the isolated RNA may be subsequently analyzed using molecular biology applications that are known to be sensitive to contaminants, such as reverse transcriptase polymerase chain reaction (RT-PCR) and microarray analysis.

SUMMARY OF THE INVENTION

To address these and other problems in the prior art, one aspect of the present invention is a device for isolating RNA from a sample containing white blood cells. The device includes a device body having an inlet port for receiving a sample containing white blood cells, a first chamber that includes a first membrane that selectively binds white blood cells and a second chamber that includes a second membrane that reversibly binds RNA. A valve fluidly couples the first and second chambers. An outlet port is included on the device for dispensing the isolated RNA. The device further includes at least one reagent port for fluidly coupling at least one of the first and second chambers to at least one reagent reservoir; and at least one waste port for fluidly coupling at least one of the first and second chambers to a waste receptacle coupled to a vacuum source. In one embodiment, the disposable device further includes a third thermal reaction chamber, the temperature of which is controlled by an external source.

In another aspect, the present invention provides a system for isolating RNA from a sample containing white blood cells, the system comprising a device having a device body with an inlet port for receiving a sample containing white blood cells, a first chamber that includes a first membrane that selectively binds white blood cells and a second chamber that includes a second membrane that reversibly binds RNA. A valve fluidly couples the first and second chambers. An outlet port is included on the device for dispensing the isolated RNA. The device further includes at least one reagent port for fluidly coupling at least one of the first and second chambers to at least one reagent reservoir; and at least one waste port for fluidly coupling at least one of the first and second chambers to a waste receptacle coupled to a vacuum source. The system also includes a control unit comprising a manifold for fluidly coupling the at least one chamber to the at least one reagent reservoir and to the at least one waste receptacle, the control unit controlling the fluid flow on the device; and a reagent reservoir comprising at least one reagent for isolating RNA, the reagent reservoir removably attached to the control unit.

In another aspect, the present invention provides a method of purifying RNA from whole blood. The method includes the steps of introducing a sample of whole blood into an inlet of a device and capturing the white blood cells on a first membrane in the device; wherein the first membrane binds white blood cells and does not substantially bind red blood cells. The method includes the step of washing the first membrane comprising captured white blood cells with a first wash buffer to remove the red blood cells; lysing the captured white blood cells with a lysis buffer to produce a lysate comprising white blood cell RNA; and capturing the white blood cell RNA in the lysate on a second membrane in the device; wherein the second membrane reversibly binds the white blood cell RNA in the presence of the lysis buffer. The second membrane is washed with a second wash buffer to remove the lysis buffer; and dried to produce RNA that is reversibly bound to the second membrane in the device.

The various embodiments of the devices, systems and methods of the present invention may be used by any user who would benefit from devices, systems and methods for purifying nucleic acid material from whole blood, such as, for example, manufacturers and retailers of medical and/or research equipment, physicians, researchers, and other medical professionals.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Unless specifically defined herein, all terms used herein have the same meaning as would be understood by those of ordinary skill in the art of the present invention.

Generally described, the present invention provides devices, systems, and methods for isolating RNA from a sample containing white blood cells, such as whole blood. The devices, systems, and methods utilize a plurality of chambers, inlets, valves, membranes, pumps, liquid barriers and other elements arranged in various configurations to manipulate the flow of a fluid sample in order to isolate RNA from such a sample. All the steps of the method of isolating RNA from whole blood are performed on the device without the need for centrifugation. The isolated RNA is recovered from the device without requiring disassembly of the device. In some embodiments, the invention provides an RNA isolation device and system that is capable of drawing a blood sample from a subject, isolating RNA from the blood sample, performing at least one diagnostic assay with the isolated RNA and providing a signal indicative of the status of the isolated RNA. In some embodiments, the device includes a unique identifier that is scanned and included in a database associated with a control unit in the system device.

The methods, device and system provide isolated RNA that is substantially purified from contaminants and capable of use in analytical methods that are known to be sensitive to contaminants, such as reverse transcriptase polymerase chain reaction (RT-PCR) and microarray analysis. The use of a self-contained closed device for white blood cell capture, lysis, RNA isolation, and optional analysis minimizes risk of exposure to blood-borne pathogens that may be present in the blood sample. The isolation and stabilization of RNA bound to a membrane in the device allows for storage of RNA containing devices at ambient temperature, thereby allowing the device to be shipped to locations remote from a research facility at a lower cost.

In the following description, certain specific embodiments of the present devices and methods are set forth, however, persons skilled in the art will understand that the various embodiments and elements described below may be combined or modified without deviating from the scope of the invention.

Figure 1:
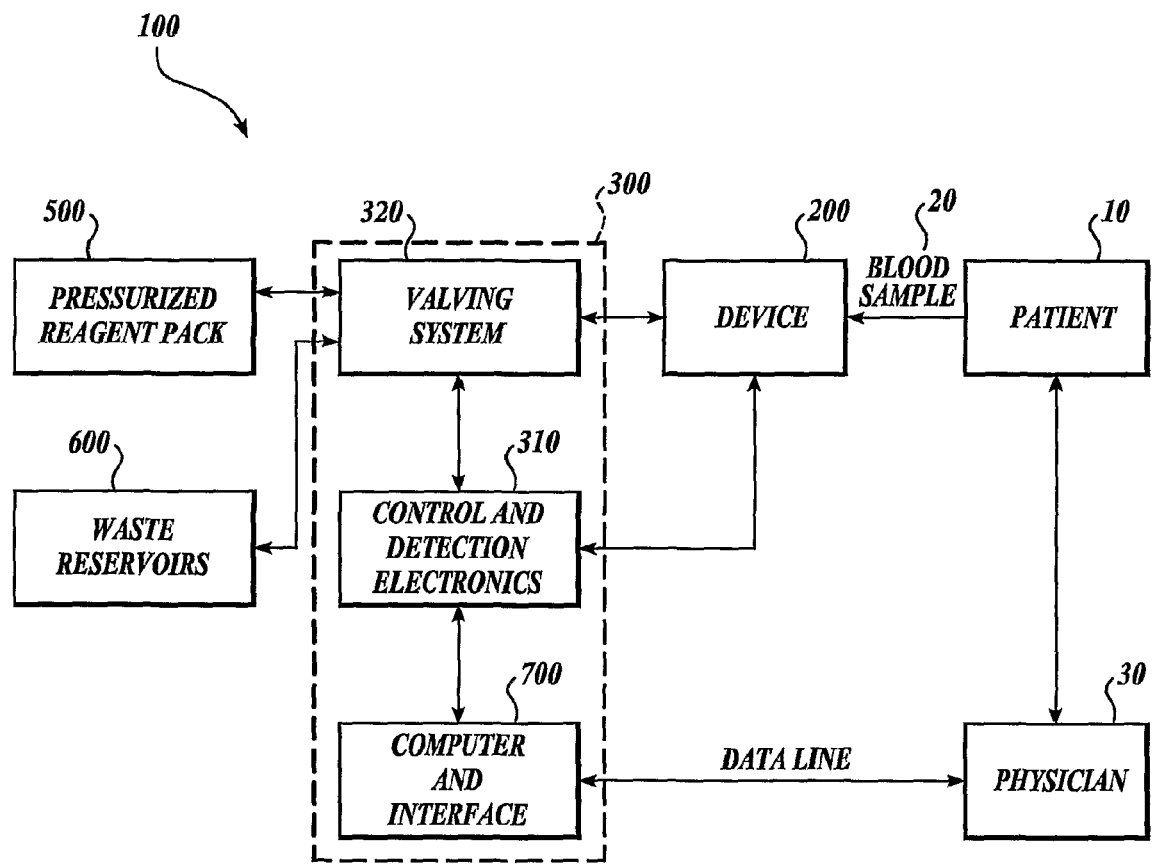
FIG. 1 illustrates a flowchart of an RNA isolation system including a disposable RNA isolation device, a control unit, and reagent pack in accordance with an embodiment of the present invention.

FIG. 1 illustrates the components of an exemplary RNA isolation system 100 having a disposable RNA isolation device 200 according to one embodiment of the present invention. The major components of the RNA isolation system 100 include a disposable RNA isolation device 200, a reagent pack 500, and a waste reservoir 600 that are each removably attached to a control unit 300. The disposable RNA isolation device 200 has a device body that includes a series of chambers having one or more membranes included therein for the capture of white blood cells from whole blood and isolation of RNA therefrom, as described in more detail below. In some embodiments, the disposable RNA isolation device 200 also includes a reaction chamber suitable for amplification and analysis of the isolated RNA. The control unit 300 includes a valving system 320 that controls valves connecting the various chambers in the device 200 to a removable reagent pack 500 and to the one or more waste reservoirs 600. In one embodiment, the disposable RNA isolation device 200 includes at least one waste reservoir disposed within the device body in order to provide a self-contained, disposable device to reduce the risk of exposure to biohazardous material. The valving system 320 is controlled by control and detection electronics 310 associated with the control unit 300. The control unit 300 also includes a computer 700 with an optional connection to a network 800.

In operation of the system 100, a physician 30, or other medical personnel, removes a sample containing white blood cells, such as a blood sample 20 from a patient 10. The blood sample 20 is introduced into the disposable RNA isolation device 200 either prior to, or after, the device 200 is attached to the control unit 300. The reagent pack 500 and waste reservoir(s) 600 are also attached to the control unit 300 prior to operating the system. The control and detection electronics 310 control the fluid flow required for the processing of the blood sample 20 in the device 200 as described in more detail below. In some embodiments of the system 100, the isolated RNA is removed from the device 200 by the physician 30 or other medical or lab personnel and analyzed using molecular biology assays external to the device. In other embodiments of the system 100, the RNA is stabilized on a membrane within the device 200 prior to shipment to a remote location where the RNA is eluted and analyzed. In further embodiments of the system 100, the disposable device 200 includes a reaction chamber disposed within the device body for performing on-board amplification and analysis of the isolated RNA.

Figure 2:
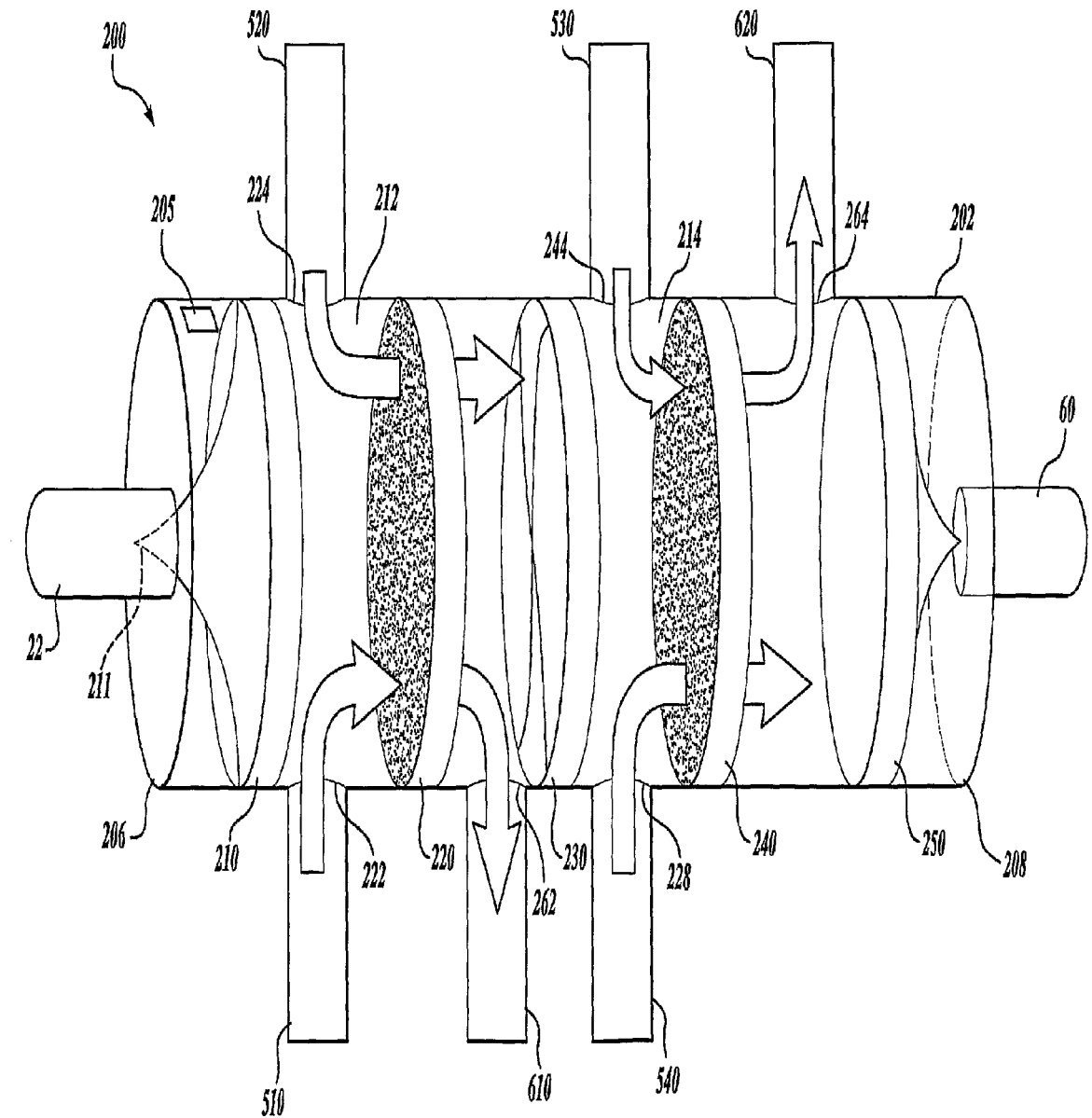
FIG. 2 is a schematic diagram of a representative disposable RNA isolation device having a first chamber and a second chamber in accordance with an embodiment of the present invention.

FIG. 2 illustrates one embodiment of the disposable RNA isolation device 200. As shown, the device 200 has a device body 202 with a first end 206 having a sample inlet port 210 adapted to interface with a blood collection tube 22 and a second end 208 having an RNA outlet port 250 adapted to interface with an RNA collection tube 60. The blood collection tube 22 contains a sample of whole blood which may be collected using any manner known, for example, using EDTA as an anticoagulant. An exemplary type of blood collection tube is a standard evacuated tube, i.e., a Vacutainer tube. In one embodiment, the blood tube 22 has a set of retention pockets that are snap-fitted into place with a set of corresponding latch arms (not shown) in the inlet port 210 to form a secured connection. In the embodiment shown in FIG. 2, the inlet port 210 in the device 200 includes at least one vented transfer spike 211 capable of piercing the rubber closure of the blood collection tube 22. In operation, a blood sample (e.g., from 2.5 to 3 ml) is drawn into the evacuated blood collection tube 22. The blood collection tube 22 is then attached to the inlet port 210 of the device 200. The blood may be transferred without opening the blood collection tube 22 by using the vented transfer spike 211 inserted through the stopper of the blood collection tube 22.

In another embodiment of the device 200, the inlet port 210 is adapted to removably attach to, or receive, a blood draw apparatus, such as a butterfly needle (not shown) or other type of needle, to allow a blood sample to be drawn directly from a subject into the inlet port 210 of the device 200 by applying a vacuum via an evacuated chamber, through the use of a push/pull mechanism such as a syringe, or using a vacuum source controlled by the control unit 300.

In the embodiment of the device 200 shown in FIG. 2, the device body 202 surrounds a first chamber 212 and a second chamber 214 that are fluidly coupled by a valve 230. The first chamber 212 includes a first membrane 220 that selectively binds white blood cells. The second chamber 214 includes a second membrane 240 that reversibly binds RNA. The device body 202 further includes a series of reagent ports that interface with the reagent pack 500 in the system 100 for the delivery of processing reagents and one or more waste ports that interface with the waste receptacle 600 for the removal of blood and waste products, as described in more detail below. The device body 202 may be formed into any shape suitable for removable attachment to the control unit 300. In one embodiment, the device body 202 is formed into a substantially rectangular shape, such as the shape of a credit card that is approximately 10 cm×4 cm×0.5 cm in dimension.

With continued reference to FIG. 2, the valve 230 that separates the first chamber 212 and the second chamber 214 is controlled by the control electronics 310 associated with the control unit 300 and may be of any suitable construction and use any actuation principles, e.g., hydraulic, pneumatic, mechanical (e.g., a shutter valve, band restriction around a passageway, magnetic, etc.). In one embodiment of the device 200, the first chamber 212 and the second chamber 214 are sealed vacuum chambers. In accordance with this embodiment, the first membrane 220 and the second membrane 240 are integrated into the first 212 and second chamber 214, respectively to form a substantially air tight seal with the walls of the chamber. In one embodiment, the valve 230 is a shutter valve movably affixed between the chambers 212 and 214. When the shutter valve 230 is in a closed position, and a waste port 262 leading to the first chamber is opened, vacuum is maintained within the first chamber 212 and fluid is drawn into the waste receptacle 610. When the shutter valve is in an open position, and a waste port 264 leading to the second chamber 214 is opened, vacuum is maintained within the first chamber 212 and the second chamber 214, causing fluid to be drawn from the first chamber 212 into the second chamber 214, through the second membrane 240, and into the waste port 620. The vacuum pressure should be of sufficient force in a given configuration to pull the fluid completely across the membrane within about 30 seconds, such as in the range of about 1 Torr.

The vacuum source for use in the various embodiments of the device 200 and system 100 may be any suitable vacuum source capable of effecting fluidic flow through the chambers 212 and 214 of the device 200 via positive pressure, negative pressure, or a combination of positive and negative pressure. Exemplary vacuum sources include, but are not limited to: an evacuated chamber, an automated vacuum source controlled by the control unit 300, a manually operated vacuum source, a push/pull mechanism such as a syringe, or any combination of the above.

In the embodiment of the device 200 shown in FIG. 2, the first chamber 212 includes the first membrane 220 that selectively binds white blood cells, a first wash buffer port 222, and a first lysis buffer port 224 located upstream of the first membrane 220. Also included in the first chamber 212 is a first waste port 262 located downstream of the first membrane 220. The first wash buffer port 222 and the first lysis buffer port 224 are adapted to removably attach to fluid lines that are in selective fluid communication with a wash buffer reservoir 510 and a lysis buffer reservoir 520, respectively, as shown more clearly in FIG. 7. The first waste port 262 is adapted to removably attach to a blood waste receptacle 610 associated with a vacuum source. In some embodiments of the device 200, the blood waste receptacle 610 is external to the device body 202. In other embodiments, the blood waste receptacle 610 is contained within the device body 202, in order to provide a disposable device that minimizes the operator's risk of exposure to biohazardous materials.

The first membrane 220 may be any membrane or fibrous matrix capable of selectively binding white blood cells (WBC) such as leukocytes from whole blood, while allowing red blood cells, blood plasma, and other non-WBC blood components to pass through as waste material. Exemplary membranes suitable for use as the first membrane 220 are the leukocyte depletion fibrous matrices sold by Pall Corporation, under the name Leukosorb® Medium, such as matrices having a port size of 8.0 μM and a filter thickness of from 14.0-20.0 mm. Leukosorb® is a fibrous medium that was originally designed for the depletion of WBCs from blood for transfusion. Descriptions of the Leukosorb® membranes and their use may be found in U.S. Pat. Nos. 5,501,795; 5,100,564; 4,880,548; 4,923,620; 4,925,572; 5,229,012; 5,344,561 and U.S. Patent Application No. 20030134417, which are incorporated herein by reference. In some embodiments, the first membrane 220 included in the device 200 is capable of capturing WBCs from a sample of whole blood ranging in volume from about 2 mL to about 3 mL. The whole blood may be passed through the first membrane 220 by applying a vacuum across the membrane, or by applying a pressure gradient via a pump across the membrane.

With continued reference to FIG. 2, in the embodiment shown the second chamber 214 includes a second membrane 240 that reversibly binds RNA, a second RNA wash buffer port 244, and an RNA elution port 228 upstream of the second membrane 240. The second membrane 240 may be any membrane or matrix that is capable of reversibly binding RNA. For example, a glass-fiber filter for RNA binding and elution, such as Type A/E, Type A/B, Type A/C, Type A/D, Extra Thick Metrigard™ Discs, or TCLP Glass Fiber Filters (commercially available from Pall Corporation), or Glass Fiber filter AP408X105 (commercially available from Millipore).

Also included in the second chamber 214 is a second waste port 264 downstream of the second membrane 240. The second RNA wash buffer port 244 and the RNA elution port 228 are adapted to removably attach to fluid lines that are in selective fluid communication with a second RNA wash buffer reservoir 530 and an RNA elution buffer reservoir 540, respectively, as shown more clearly in FIG. 7. The second waste port 264 is adapted to removably attach to a second waste receptacle 620.

The device 200 and system 100 allow for the isolation of RNA from a sample in a relatively short period of time, such as in a period of time less than 30 minutes, such as less than 20 minutes, or less than 10 minutes, as measured from the time of receiving the sample into the device up to the step of binding RNA to the second membrane.

Figure 3:
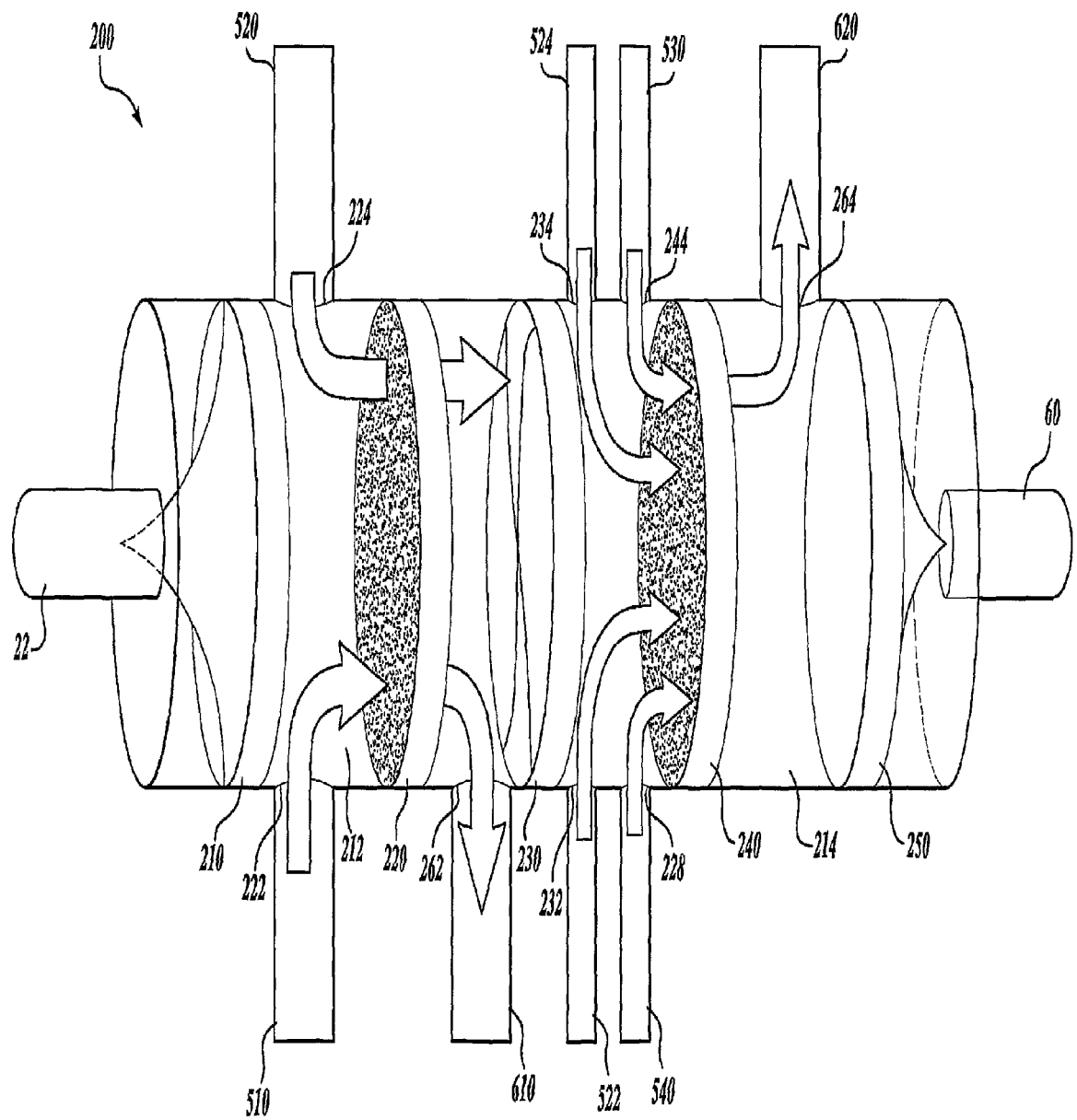
FIG. 3 is a schematic diagram of another representative disposable RNA isolation device having a first chamber, a second chamber and a plurality of reagent ports in accordance with an embodiment of the present invention.

FIG. 3 illustrates an alternative embodiment of the disposable RNA isolation device 200, having features that are substantially similar to the embodiment of the device shown in FIG. 2 with additional features as will now be described. As shown in FIG. 3, the second subchamber 214 includes an RNA binding buffer port 234, and RNA wash buffer port 244, a DNAse buffer port 232, and an RNA elution buffer port 228 upstream of the second membrane 240. The second chamber 214 further includes a waste port 264 downstream of the second membrane 240. In operation of this embodiment of the device 200, the white blood cell lysate enters the second chamber 214 through the valve 230, and is then mixed with an RNA binding buffer pumped through the port 234. The lysate and binding buffer mixture are then pulled through the second membrane 240 under a vacuum. The RNA is bound to the membrane, and the waste material is pulled through the waste port 264 into the waste receptacle 620.

Figure 4:
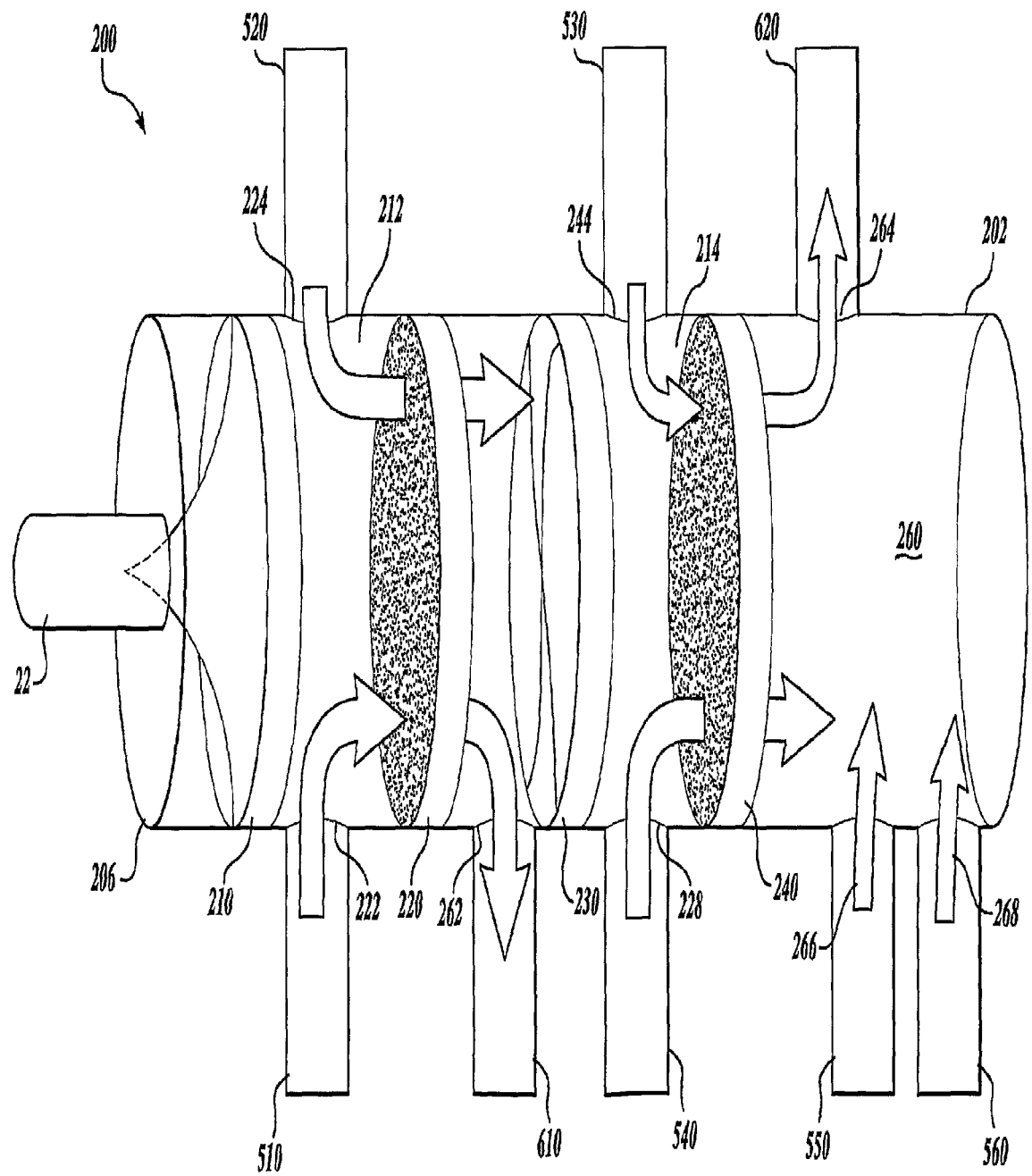
FIG. 4 is a schematic diagram of another embodiment of a disposable RNA isolation and diagnostic device having a thermal reaction chamber in accordance with another embodiment of the present invention.

FIG. 4 illustrates yet another embodiment of the disposable RNA isolation device 200 comprising a device body 202 that includes a first end 206 having a blood input port 210, a first chamber 212 including a first membrane 220 that selectively binds white blood cells, a second chamber 214 including a second membrane 240 that reversibly binds RNA, and a third thermal chamber 260 having thermal conductivity in order to rapidly change temperatures during reactions requiring temperature cycling. The chambers 212 and 214 are substantially similar to those previously described above in reference to FIG. 2 and FIG. 3. The thermal chamber 260 shown in FIG. 4 is made of plastic materials such as medical grade polyvinyl chloride, or high density polyethylene designed for efficient heat transfer, with at least a portion of the chamber adapted to contact or be placed adjacent to an external heat source, causing a change in the temperature of the chamber 260. In one embodiment of the device 200, the third chamber 260 has a wall thickness on the order of about 1 mm in order to allow an external heat source to vary the temperature between 4° C. and 100° C. In the embodiment shown in FIG. 4, the third thermal chamber further includes reagent ports 266 and 268 for importing reverse transcriptase master mix and PCR master mix, respectively.

Figure 5:
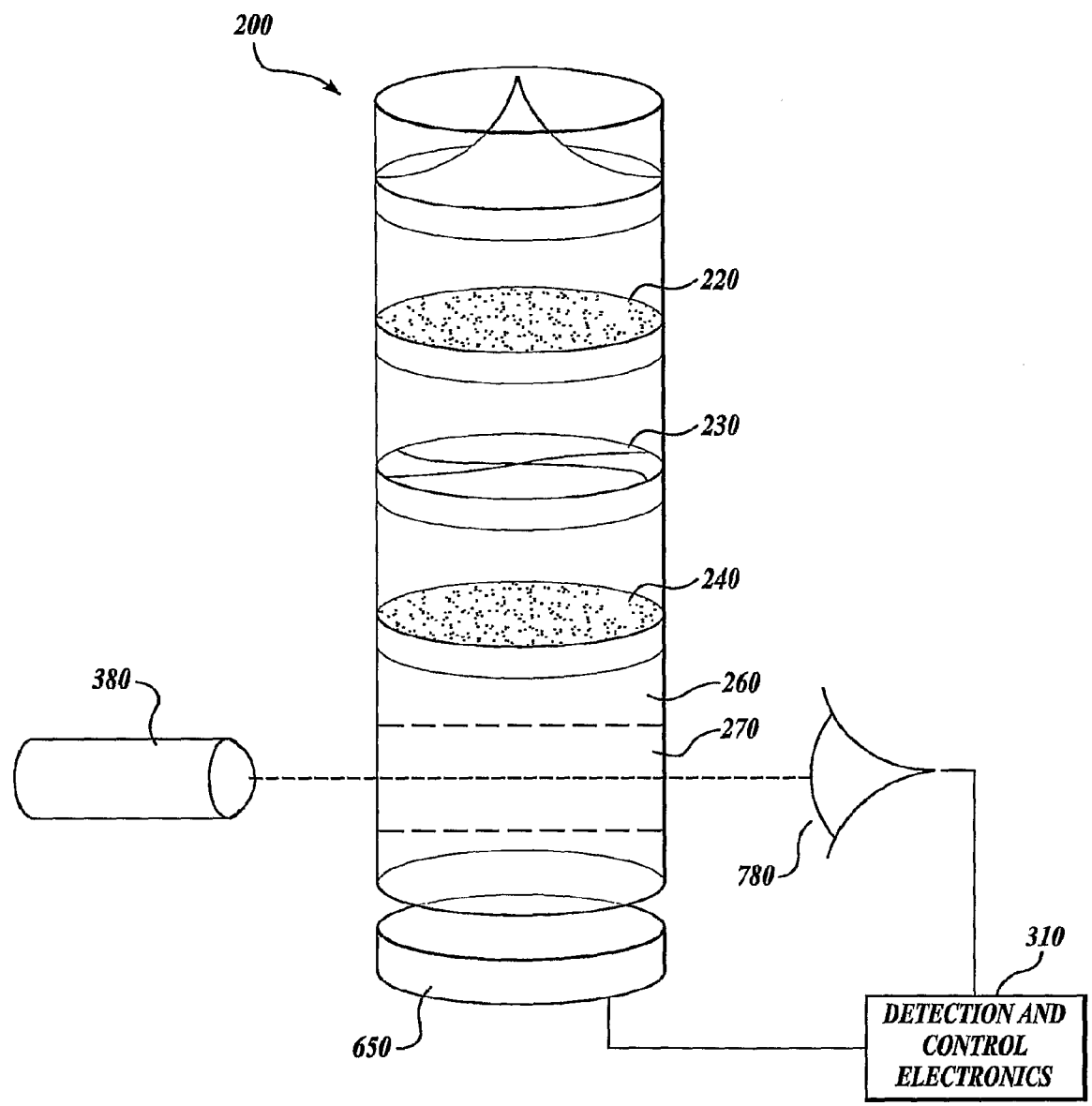
FIG. 5 is a schematic diagram of a disposable RNA isolation and diagnostic device inserted into a control unit having a signal detector.

As shown best in FIG. 5, the third thermal chamber 260 is positioned adjacent an external temperature control unit 650, such as a Peltier device that is controlled by the control electronics 310 associated with the control unit 300. In some embodiments, the third thermal chamber 260 also includes a detection window 270, such as a transparent window that allows an external detector unit 780 to detect a signal indicative of at least one feature of the isolated RNA, such as the emission of a wavelength characteristic of a fluorophore. Nonlimiting examples of other suitable signal detection systems include chemiluminescence, bioluminescence, absorbance, and fluorescence polarization. In one embodiment of the system 100, as shown in FIG. 1 and FIG. 5, a light source 380, such as a laser may be used to stimulate a fluorophore that has been incorporated into amplified nucleic acid material, thereby producing a fluorescent emission which is then detected by the signal detector 780 and transmitted to the control unit 300. Such fluorescence laser scanning devices are described, e.g., in Schena et al., *Genome Res* 6: 639-645 (1996). The data indicative of the status of the RNA is then recorded, either manually, or via detection electronics in the system 100.

The various embodiments of the device 200 may be manufactured out of materials that are compatible with solutions and materials used for the isolation, amplification and analysis of RNA, and that also will not dissolve, abrade or otherwise interfere with the quality of the isolated RNA. Suitable materials include, but are not limited to medical grade polyvinyl chloride and high density polyethylene.

In accordance with the operation of the RNA isolation system 100, as shown in FIG. 1, the disposable device 200 is removably inserted into an interface in the control unit 300 in a manner that forms a secured connection, such as with the use of a latch arm. The control unit 300 is a self-contained, mechanical and electrical device designed to interface with the device 200 and the reaction pack 500 to control the valving and vacuum in the device 200. The control unit 300 may also include operator interface features such as a user input device (e.g., keyboard), control buttons, LED indicator lights, an audio tone for verifying operational status, and a means for indicating if sufficient reagents remain in the reagent pack 500 for processing a blood sample. In some embodiments, the control unit 300 is manufactured to be a portable, inexpensive device (e.g., less than $500) in order to provide ease of use in settings such as a doctor's office, clinic or academic settings. For example, in one embodiment the size of the control unit 300 is approximately 23 cm (W)×18 cm (H)×25 cm (D).

Figure 6:
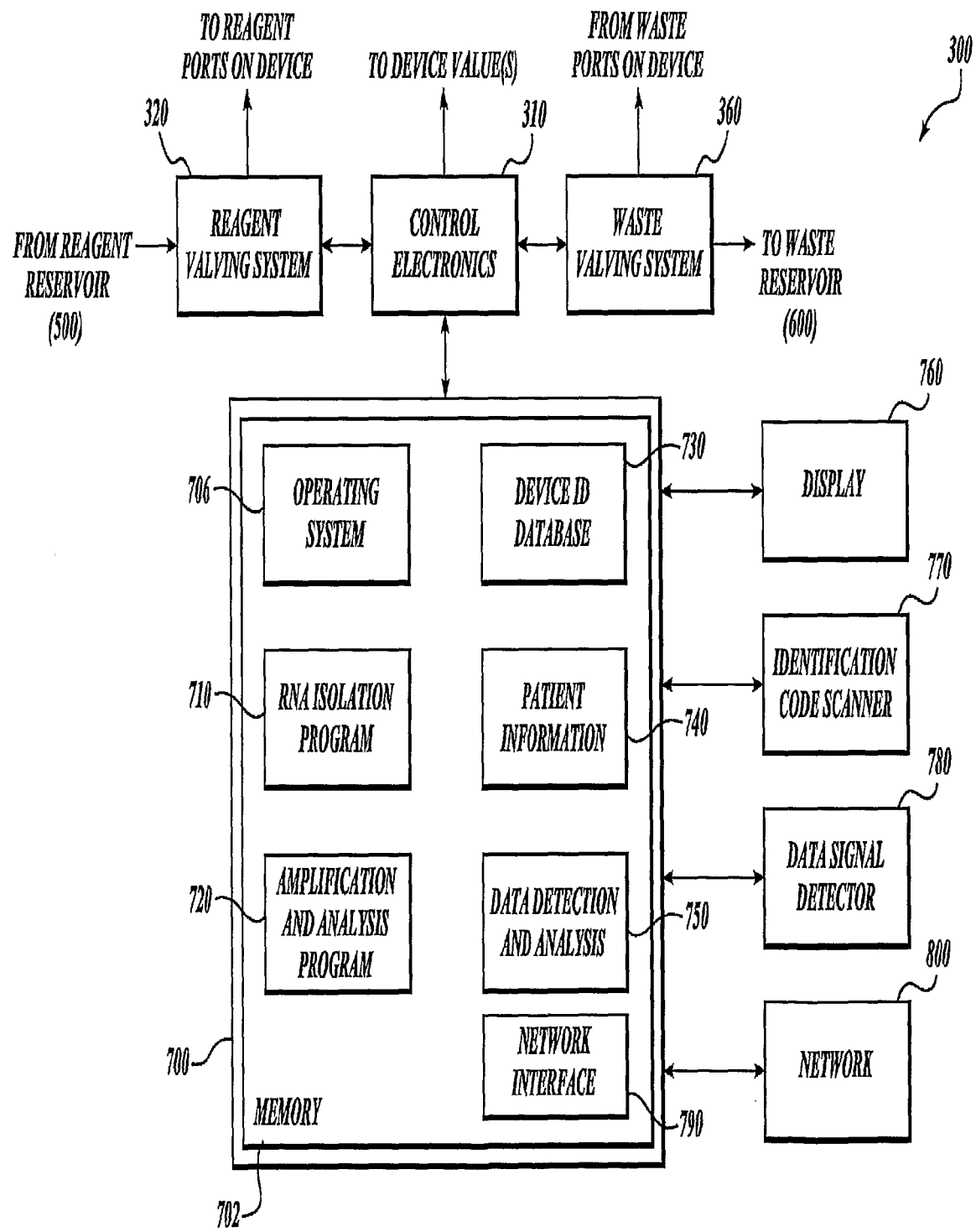
FIG. 6 is a block diagram of a representative control unit for use in an RNA isolation system in accordance with an embodiment of the present invention.

FIG. 6 is a block diagram of an illustrative architecture for the control unit 300 containing a computer 700 in accordance with the system 100 of the invention. Those of ordinary skill in the art will appreciate that the computer 700 may include additional components. However, it is not necessary that all of these generally conventional components be shown in order to disclose an illustrative embodiment of the invention. As shown in FIG. 6, the exemplary embodiment of the control unit 300 shown includes the reagent valving system 320 and the waste valving system 360 that are connected to the control electronics processor 310 which is in turn connected to the computer 700. Additional components that may be connected to the computer 700 include a display 760, a barcode scanner 770, a data signal detector 780 and a network 800 that can send data to a remote database or provide software upgrades to the control unit 300 from a remote location. The computer 700 includes a memory 702, an operating system 706, an RNA isolation program 710, an amplification and analysis program 720, a device identifier database 730, a patient information database 740, and a data detection and analysis program 750. The memory 702, display 760, barcode scanner 770, data signal detector 780, network interface 800, reagent valving system 320 and waste valving system 360 are all connected to the control electronics processor 310 via a bus.

The memory 702 generally comprises a random access memory ("RAM"), a read-only memory ("ROM") and a permanent mass storage device, such as a hard disk drive, tape driver, optical drive, floppy drive, CD-ROM, DVD-ROM or removable storage drive. Other peripherals may also be connected to the control electronics and processor in a similar manner. Although the embodiment of the computer 700 shown in FIG. 6 contains an amplification and analysis program 720 and a data detection and analysis program 750, these features are optional and not required in some embodiments of the invention. In some embodiments of the invention, the amplification and analysis program 720 controls a heat source 650 (shown in FIG. 5) that is connected to, or provided adjacent to, the third thermal reaction chamber 260 in the device 200 in order to expose the third chamber to a thermal amplification temperature profile. The heat source 650 may be any suitable heat source capable of varying the temperature profile of the third chamber 260 of the device 200 between a temperature range of 4° C. to 100° C. Suitable heat sources include, for example, a flat metal resistor, infrared heating, radiant heating, a Peltier heater, liquid heating and the like.

The reagent valving system 320 and the waste valving system 360 on the control unit 300 interfaces with a manifold and/or fluid lines that removably attach to the reagent and waste ports on the device 200. The valving systems 320 and 360 have a select number of solenoid-operated pneumatic valves that control pressure and vacuum delivered to the chambers in the device 200, as further described below. The control unit 300 includes pump assembly electronics that contain the motor controller hardware for controlling the individual motors used to operate the pumps and the pneumatic valves.

Figure 7:
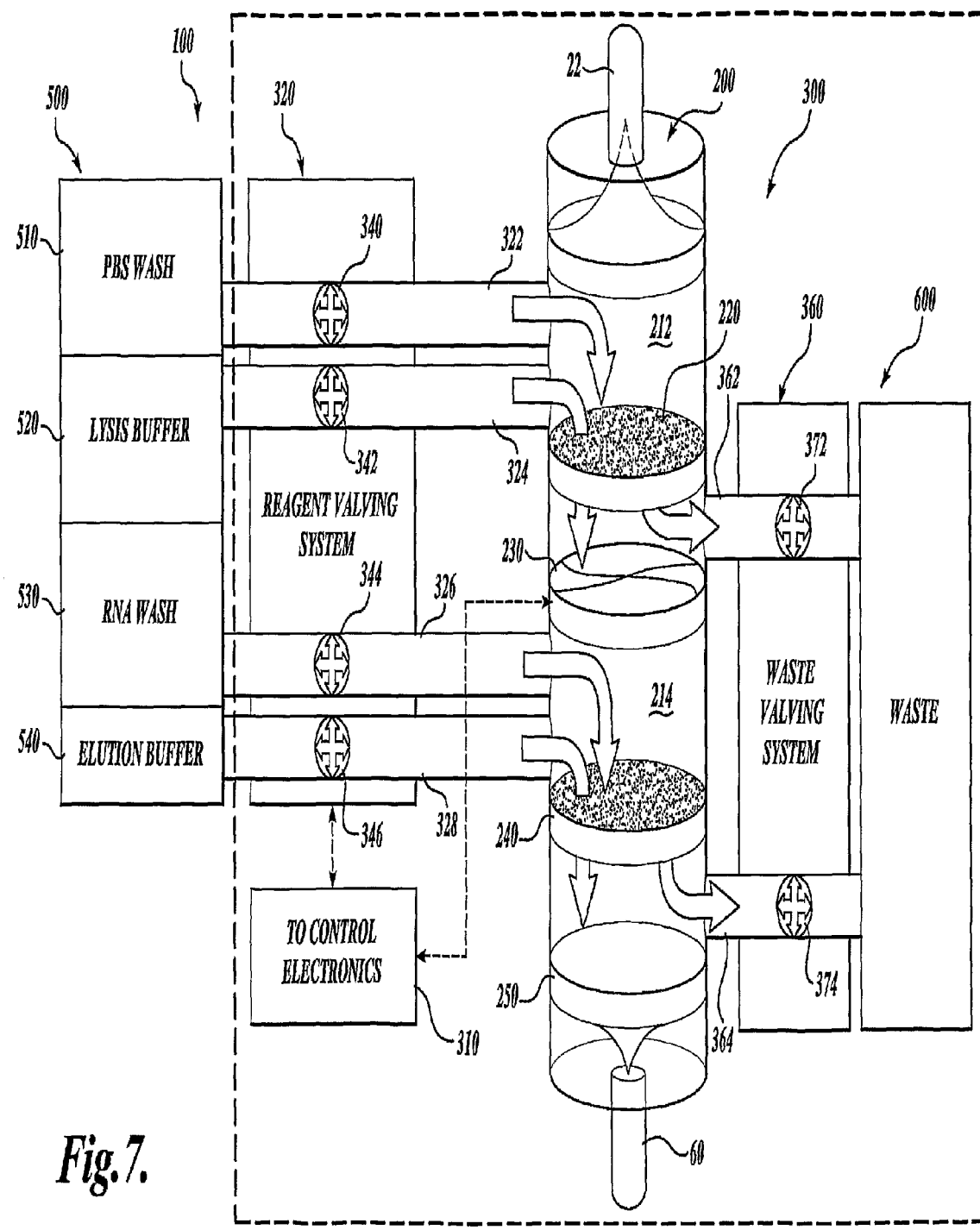
FIG. 7 is a schematic diagram of an embodiment of the RNA isolation system including an RNA isolation device having a first chamber and a second chamber.
Figure 8:
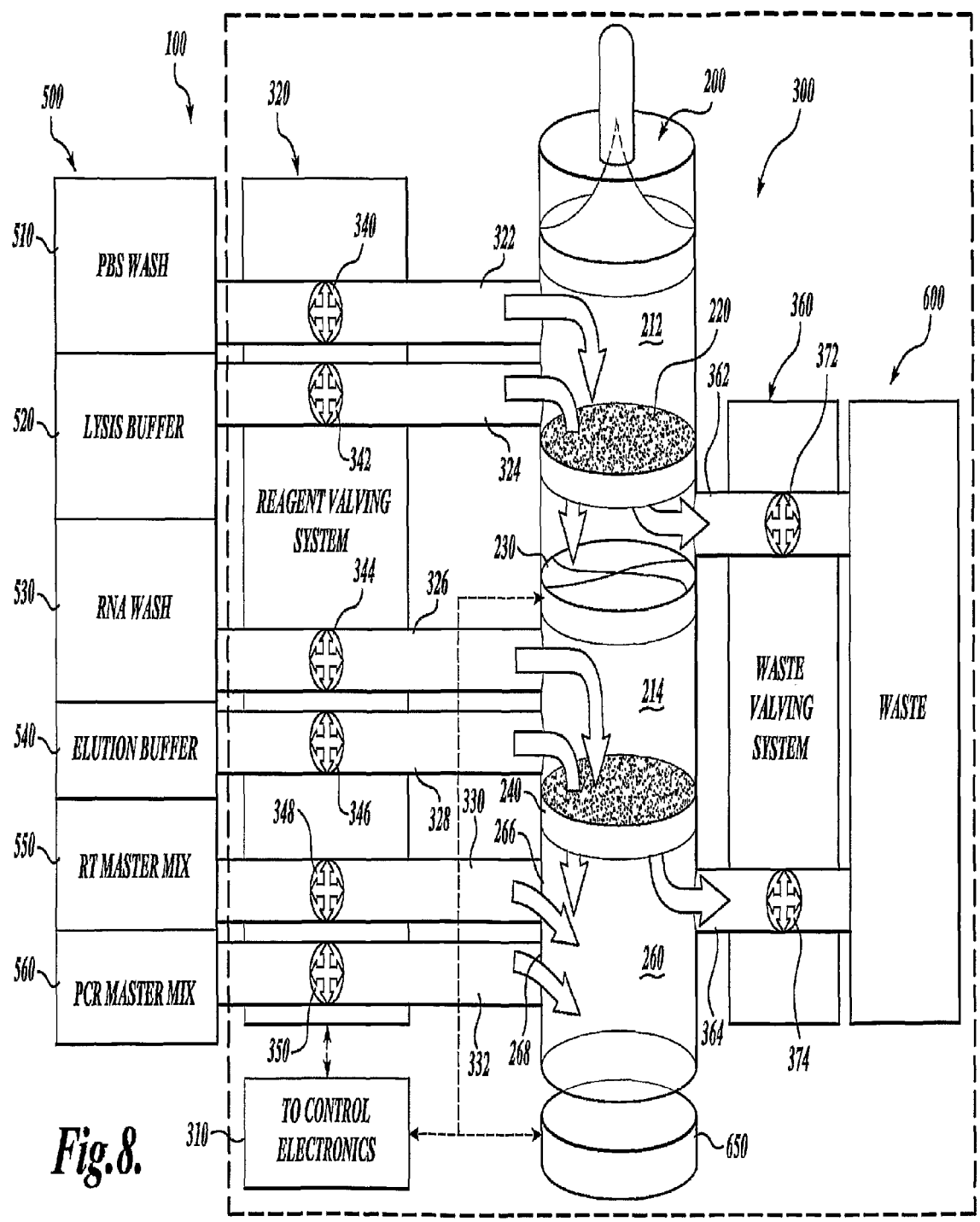
FIG. 8 is a schematic diagram of another embodiment of the RNA isolation system including an RNA isolation device having a thermal reaction chamber.

The reagent pack 500 is a disposable cartridge containing one or more reservoir compartments having solutions and reagents for isolating RNA from blood, and optionally for conducting analytical assays on the isolated RNA. The reservoir compartments in the reagent pack have the capacity to hold a volume of solutions and reagents sufficient to process at least 2 or more devices, such as up to 10 or more devices. In one embodiment, as shown in FIG. 7, the reagent pack 500 comprises the following compartments: PBS wash buffer 510, lysis buffer 520, RNA wash buffer 530 and RNA elution buffer 540. In another embodiment as shown in FIG. 8, the reagent pack 500 comprises the following compartments: PBS wash buffer 510, lysis buffer 520, RNA wash buffer 530, elution buffer 540, Reverse transcriptase (RT) master mix 550, and PCR master mix 560. In additional embodiments, the reagent pack 500 may comprise one or more additional reagents used to isolate RNA and/or analyze RNA, such as RNA binding buffer, DNAse buffer, and the like.

The lysis solution used to lyse the WBC captured on the second membrane 240 comprises a chaotropic agent such as a guanidinium salt (e.g., guanidine hydrochloride, guanidinium thiocyanate, guanidinium isothiocyanate), sodium iodide, sodium perchlorate or sodium trichloroacetate. The RNA binding buffer may be any binding buffer typically used with a silica matrix, such as non-chaotropic salts (sodium, calcium, lithium or potassium) and ethanol; or a chaotropic salt and ethanol. Exemplary reagents and solutions suitable for use in the invention are provided below in TABLE 1.

TABLE 1

| Buffer | Components | Volume (per 2.5 ml of whole blood) |
| --- | --- | --- |
| PBS Wash | phosphate buffered saline, pH 7.4 | 100 µl to 1000 µl |
| Lysis buffer | SV RNA Lysis Buffer, (product code Z305, Jun. 16, 2003) (Promega, Madison WI): guanidinium thiocyanate, β-Mercaptoethanol | 100 µl to 1000 µl |
| RNA binding buffer | Zymo Research, product code R1013-2, Feb. 23, 2006 (Orange, CA) | 100 µl to 1000 µl |
| RNA Wash buffer | Zymo Research, product code R1013-3-6, Feb. 23, 2006 (Orange, CA) | 100 µl to 1000 µl |
| DNAse buffer | Qiagen, product code 79254, Feb. 23, 2006 (Valencia, CA) | 100 µl to 1000 µl |
| RNA Elution buffer | nuclease-free water | 50 µl to 100 µl |

Reagent supply lines run from each compartment in the reagent pack 500 through the reagent valving system 320 to a corresponding reagent port on the device 200. The reagent valving system 320 is controlled by control electronics 310 associated with the instrument 100. The control electronics 310 are also electrically connected to the device and control the operation of the shutter valve 230 in the device 200. With reference to FIG. 6, the system 100 also includes at least one waste receptacle 600 that is in fluid communication with the device 200 via a waste valving system 360 controlled by the control electronics 310 associated with the control unit 300.

With reference now to FIG. 7, in operation of the system 100, a blood sample 22 is introduced into the first chamber 212 of the device 200. A first waste export valve 372 is opened, allowing fluid communication between the first chamber 212 of the device 200 and the waste receptacle 600 attached to a vacuum source, thereby drawing the blood sample through the first membrane 220. The non-WBC portions of the blood sample are drawn through the waste line 362 into the waste receptacle 600. A first reagent import valve 340 is opened, allowing PBS wash buffer in the reagent compartment 510 to flow through a reagent line 322 into the first chamber 212 and wash over the captured WBC on the first membrane 220. The waste export valve 372 is kept in the open position, allowing the PBS wash buffer to flow through the waste line 362 into the waste receptacle 600. The waste export valve 372 is then closed. The shutter valve 230 inside the device 200 that separates the first chamber 212 from the second chamber 214 is then opened via the control electronics 310. A second waste export valve 374 is also opened to allow fluid communication between the first chamber 212 and the second chamber 214 of the device 200 and the waste receptacle 600 attached to the vacuum source. A second reagent import valve 342 is opened, allowing lysis buffer to flow from the reagent compartment 520 through a reagent line 324 into the first chamber 212 of the device 200. The lysis buffer is passed over the first membrane 220, thereby contacting and lysing the captured WBC on the first membrane 220 to create a WBC lysate. The WBC lysate is drawn into the second chamber 214 and passes over the second membrane 240 which reversibly binds RNA contained in the WBC lysate.

An optional step may be added in which an RNA binding buffer contained in an additional compartment of the reagent pack (not shown), is introduced through an additional port into the second chamber 214 at substantially the same time as the WBC lysate, in order to improve the efficiency of RNA binding to the second membrane 240. The non-captured portion of the WBC lysate and optional RNA binding solution flows through the waste line 364 into the waste receptacle 600. The waste export valve 374 is kept in the open position and a third reagent valve 344 is opened to allow RNA wash buffer to flow into the second chamber 214 and over the second membrane 240 to remove cellular debris. An optional step may be added in which a DNAse buffer contained in an additional compartment of the reagent pack (not shown) is introduced through an additional port into the second chamber 214 and passed over the second membrane in order to remove any contaminating DNA present on the membrane. After the desired reagents are passed over the second membrane, the valve 374 is left open for about 30 to 60 seconds in order to dry down the bound RNA such that it is stabilized on the membrane. The RNA may then be eluted from the second membrane by opening the elution buffer import valve 346, allowing elution buffer to pass over the second membrane, thereby eluting the bound RNA into a recovery tube 60 positioned over the outlet port 250.

Alternatively, once the RNA is bound to the second membrane, the device 200 containing the bound RNA is removed from the control unit 300, packaged, stored, and optionally shipped to a remote site, such as a central processing laboratory prior to elution of the RNA.

In some embodiments, the device comprising RNA bound to the second membrane 240 is stored at ambient temperature for a period of time prior to RNA elution. For example, this storage time may be minutes, hours, days, weeks, months or longer.

In an alternative embodiment, the RNA is eluted from the second membrane 240 and assayed within the device 200 during connection to the control unit 300. With reference to FIG. 8, the operation of the system 100 up to the elution of the RNA from the second membrane is substantially the same as that described above in reference to FIG. 7. As shown in FIG. 8, the RNA is bound to the second membrane 240. The RNA is then eluted from the second membrane 240 by opening the elution buffer import valve 346, allowing elution buffer to pass over the second membrane, thereby eluting the bound RNA into the third thermal chamber 260.

After the second membrane 240 in the device is dried under a vacuum, the second waste valve 374 is closed and an elution buffer is passed over the second membrane 240 and collected in a sealed reaction chamber 260 housed in the device. The RNA is then analyzed by RT-PCR as follows: The reagent input valve 348 is opened and 10 µl to 100 µl of RT mix is added via a reagent line 330 to the third thermal chamber. The chamber 260 is heated by a Peltier device 650 associated with the control unit to a temperature of about 42° C. for a period of time from 1 minute to 1 hour. The reverse transcriptase enzyme is then inactivated by heating the chamber to a temperature from 70° C. to 95° C. for a time period ranging from 1 minute to 10 minutes. The reaction chamber 260 is then cooled to 50° C. The reagent input valve 350 is then opened and 10 µl to 100 µl of PCR master mix with gene-specific primers are added from a reagent line 332 into the chamber 260. The temperature of the chamber 260 is then raised to about 95° C. for a time period from 1 minute to 10 minutes followed by repeated cycling through a temperature profile, such as 60° C. for 30 seconds, 72° C. for 30 seconds, 95° C. for 30 seconds. As shown in FIG. 5, a reading is taken through an optical window 270 in the reaction chamber 260 using an optical detection system such as a fluorescent light source 380 and a fluorescent reader 780 until a signal is detected above a threshold value.

In an alternative configuration, a PCR master mix is used that contains more than one gene-specific primer and the optical detection system contains optical filters or laser diodes tuned to specific wavelengths that are able to detect more than one amplified species at a time.

As exemplified in FIG. 1, after the data signal is detected and the read-out is complete, the computer 700 associated with the control unit 300 sends instructions to pass the results of the RNA analysis to a database 750 that can be accessed by a physician or remotely via the network 800 by a centralized facility, where the results may be correlated with the sample identifier and are utilized to determine a therapeutic course of action.

In various embodiments, the system 100 provides a device 200 and reagents for carrying out RT-PCR reactions for the analysis of the level of one or more mRNA species such as the levels of expression of mRNAs transcribed from one or several genes, analysis of global mRNA expression levels, analysis of expression of small endogenous RNA molecules such as micro RNAs and small interfering RNAs in the isolated RNA. In some embodiments, the sample of whole blood may be isolated from a mammalian subject that has a reduced number of WBC, such as an immunocompromised subject. In such cases, the number of captured white blood cells per mL of starting blood sample will be reduced, thereby resulting in a reduced amount of isolated RNA. Accordingly, the reaction chamber in the device may be used in connection with suitable reagents in the reagent pack for the enzymatic linear amplification of small input amounts of RNA prior to use in expression studies, microarray analysis and the like. A suitable method for linear mRNA amplification is described in U.S. Pat. No. 6,132,997, issued to Shannon, which is hereby incorporated by reference.

Other assays and detection technologies that may be carried out in the reaction chamber of the device 200 and detected by the external detector unit 780 in the system 100 include, for example, an RNA transcription-based amplification technique (NASBA) for the detection of viable *Salmonella enterica* (BioMerieux, Inc, Durham N.C., S. A. Simpkins, et al *Lett. Appl. Microbiol.,* 30: 75-79. (2000)), cDNA-mediated annealing, selection, extension, and ligation (DASL) (Illumina, San Diego, Calif. Gene Expression Profiles in Formalin-Fixed, Paraffin-Embedded Tissues Obtained with a Novel Assay for Microarray Analysis, Marina Bibikoval et al., Clinical Chem 50: 2384-2386 (2004)), Ovation (NuGEN, San Carlos, Calif., described in U.S. Pat. No. 6,692,918, US 2003/0087251 and US 2004/0005614), and the Quantigene Reagent System (Panomics, Fremont Calif., Urdea, M., et al., Branched DNA amplification multimers for the sensitive, direct detection of human hepatitis virus. *Nuc Acids Symp Ser* 24:197-200 (1991)).

The typical yield of total RNA isolated using the device 200 and system 100 of the invention can range from about 0.5 µg to about 5.0 µg from a 2.5 mL volume of whole blood. The isolated high quality RNA has at least one or more of the characteristics shown in the quality control assays listed below in TABLE 2.

TABLE 2

CHARACTERISTICS OF RNA ISOLATED USING THE RNA ISOLATION DEVICE AND SYSTEM

| Assay | Result: |
|---|---|
| A260:A280 ratio | 1.8-2.2 |
| A320 | −.01-0.01 |
| A260 max range (from triplicate read) | 0.15 |
| A320 max range (from triplicate read) | 0.02 |
| RNA 6000 Nano Assay 28S:18S ratio | >0.8 |
| RNA 6000 Nano Assay Classifier Score | 0-0.17 |
| Nonspecific Endonuclease/Nickase Activity (14-16 hr incubation of 1 µg RNA with 300 ng of supercoiled plasmid DNA, analyzed on agarose gel) | None detected |
| Exonuclease Activity (14-16 hr incubation of 1 µg RNA with 40 ng of 32P-labeled Sau3A fragments of pUC19, analyzed by PAGE) | None detected |
| Globin PCR Assay | Globin message level less than 10% of initial abundance |

The high quality RNA isolated and recovered from the RNA isolation device can be used as input for various molecular biology assays such as Northern blot, RNase protection assay, S1 nuclease protection assays, hybridization reactions and other well known RNA analysis assays. The isolated RNA may also be used in analytic assays that require contaminant free RNA, such as microarray analysis, reverse transcriptase and reverse transcriptase-polymerase chain reaction (RT-PCR). The microarray analysis using the RNA isolated according to the methods of the invention includes any analysis that requires globin message and heme contaminant-free RNA such as cDNA array, spotted oligonucleotide array, and in situ synthesized oligonucleotide array.

In some embodiments, the device 200 is labeled with an identifier 205 either prior to, or at the time of use, as shown in FIG. 2. The identifier 205 contains information regarding the device and may also include information regarding the source of the blood sample. The identifier 205 can be affixed to the device 200 at time of manufacture, or attached to the device by an operator at the time of use. The identifier 205 is in general a character string of sufficient length to uniquely characterize a single device from within large production runs. The identifier 205 may be similar to the codes used in familiar UPC barcodes (see, e.g., the Uniform Code Council, Inc., Princeton Pike Corporate Center, Lawrenceville, N.J.), or more extensive codes such as web addresses (uniform resource locators, URLs), or RFID tags.

In further embodiments, the system 100 includes an identifier recording device, such as a identification code scanner 770 associated with the control unit 300 (shown in FIG. 6). In accordance with this embodiment of the system 100, the identifier 205 on the device 200 is scanned with the scanner 770, and the computer 700 generates a record of the identifier 205. The identifier 205 may then be associated with addition information such as the model of the control unit (e.g., model number, location), time, date, patient information, and other identifiers. The identifier 205 information may be input into an identifier database 730 that is stored locally in the memory 702 of the computer 700 contained within the control unit 300. The database 730 may be downloaded over a network 800 from a remote location such as a central facility to which the device containing stored RNA will be shipped for further processing. The identifier database 730 may also contain additional information such as control unit 300 model information, RNA isolation procedure parameters and the like. In addition, information in the identifier database 730 may be associated with patient information contained in the patient information database 740. With reference to FIG. 6, those of ordinary skill in the art will appreciate that the network interface 790 includes the necessary circuitry for connecting the computer 700 directly to a LAN or WAN, or for connecting remotely to a LAN or WAN with various communication protocols, such as the TCP/IP protocol, the Internet Inter-ORB protocol, any of various wireless protocols (e.g., the IEEE 802.1x family) and the like.

As described above, in some embodiments of the system 100, information regarding a device identifier 205 and optionally additional parameters are sent to a remote location over a network 800. The use of remote processing of the RNA-containing device allows a centralized lab to process and collect and analyze data from a large number of samples, such as in a clinical trial. Moreover, the ability to notify remote facilities of the shipment of particular devices 200 allows the remote facility to track and prepare for shipment of the shipped devices. In an alternative embodiment, the RNA is eluted from the second membrane and assayed within the device 200 during connection to the control unit 300 and the data resulting from the analysis is correlated with the device identifier 205 and optional patient information and sent via the network 800 to a central facility.

In another aspect, the invention provides kits for isolating RNA from whole blood, comprising at least one packaged disposable RNA isolation device 200 (as described herein) for use in an RNA isolation system 100 (as described herein) and at least one reagent pack 500 comprising reagents for isolating RNA. In some embodiments, the kit contains multiple RNA isolation devices, such as 5, 10, 50, 100 or more devices in combination with reagent packs containing a suitable amount of reagents to support the isolation of RNA from one or more samples. For example, a single reagent pack for use in the kit may contain an amount of reagent to support the isolation of RNA from 10 samples (e.g., using 10 different devices). Nonlimiting examples of reagents for inclusion in the kits are provided in TABLE 1. In some embodiments, the kit further includes a set of identifier labels that are affixed to the devices at the time of use.

The following examples merely illustrate the best mode now contemplated for practicing the invention, but should not be construed to limit the invention.

Example 1

This Example describes a work flow process for blood collection for RNA isolation using the RNA isolation system in accordance with various embodiments of the present invention.

Collection Work Flow for Operator

Collect Blood from a subject

Number and type of blood collection tubes are specified by the study/clinical protocol.

Phlebotomist will attach coordinator-provided patient/animal identifier on tubes.

Phlebotomist will perform blood draw (either with a needle attached to the RNA isolation device, or into a blood collection tube which is attached to the RNA isolation device)

Operators will handle the control unit, RNA isolation device, and reagent pack using latex or nitrile gloves for personal safety as well as to prevent RNase contamination.

Blood collection tubes and patient ID labels will be delivered to the location of the RNA isolation system by the coordinator or other third party.

Blood collection tubes will reside at room temperature prior to processing.

The reagent pack contents are verified to contain sufficient reagents for processing the RNA isolation device.

The reagent pack barcode is scanned into a database on the computer associated with the control unit (optional).

The reagent pack is inserted into the control unit (if necessary).

The RNA isolation device is removed from packaging.

The identifier is attached to the RNA isolation device.

The device identifier is scanned into the database.

The patient/animal identification label(s) are scanned into a database (optional).

The RNA isolation device is inserted into the manifold on the control unit.

The device is secured in place on the control unit.

Verify the control unit ready indication.

Attach the blood collection Tube to the inlet port of the RNA isolation device.

Select the protocol to be run on the control unit.

Push start button.

Verify control unit processing indication.

Scan the control unit identifier code into database (optional).

Verify control unit processing complete indication (RNA is bound to second membrane)

Release latching mechanism.

Remove blood collection tube/RNA isolation device combination from control unit.

Remove blood collection tube from the RNA isolation device.

Discard the blood collection tube.

Insert the RNA isolation device containing bound RNA into a transparent storage package and seal.

Repeat steps 4 through 26 for multiple tubes.

The time to perform steps 4 through 26 is less than or equal to 30 minutes.

Discard depleted reagent packs and replace as required.

Insert packaged/sealed RNA isolation devices (containing bound RNA) into shipping container.

Ship RNA isolation devices to RNA Removal site.

Example 2

This Example describes the work flow process for the removal of RNA from an RNA isolation device in accordance with various embodiments of the present invention.

RNA Isolation Device: RNA Removal Work Flow

RNA isolation Devices containing bound RNA (produced as described in Example 1) are stored at room temperature prior to RNA Removal from the device.

Operators will handle the control unit, RNA isolation device, and reagent pack using latex or nitrile gloves for personal safety as well as to prevent RNase contamination.

Remove the RNA isolation device(s) from shipping container.

Remove the RNA isolation device from sealed package.

Remove RNA from the RNA isolation device using the control unit as follows:

Verify the reagent pack has sufficient reagent for processing the device.

Scan the reagent pack barcode into database (optional).

Insert a reagent pack into the control unit (if necessary).

Scan the device identifier into database.

Scan patient/animal identifier into database (optional).

Scan the control unit identifier into database (optional).

Insert the device into control unit.

Latch the closing mechanism.

Verify the control unit ready indication.

Push start button.

Verify control unit processing indication. Verify control unit processing complete indication.

Release latching mechanism.

Remove device from control unit.

Remove RNA in solution from device using a pipettor

Add RNA in solution to tube or microtiter plate.

Discard device in biohazard container.

Repeat steps 5(a) through 5(q) for multiple devices.

Discard depleted reagent pack and replace as required.

Operators may optionally remove RNA from the devices by robotic pipetting:

Remove RNA in solution from the devices using robotic pipette.

Add RNA in solution to individual tubes or plates using robotic pipette.

Discard devices in biohazard container.

Example 3

This example describes RNA isolation from whole blood drawn into an evacuated blood collection tube using the devices, systems and methods of the invention.

Methods:

2 to 3 mL of whole blood from a patient was collected in a Vacutainer tube (Becton Dickinson, Franklin Lanes, N.J.). The blood was introduced into an RNA isolation device via a recessed sharpie in the first end of the device (see FIG. 2). White blood cells were captured on a first membrane (Leukosorb® Pall Corporation, East Hills, N.J.) by using a vacuum to pull blood from the Vacutainer tube through the first membrane to a waste port. A wash buffer (phosphate buffered saline, pH 7.4) was then passed from a source port through the first membrane to the waste port to wash erythrocytes away from the membrane-bound leukocytes. A lysis buffer (SV RNA Lysis Buffer, Promega, Madison, Wis.) containing guanidine thiocyanate and beta-mercaptoethanol was then passed from a source port through the first membrane to release the RNA from the bound white blood cells. The lysate containing liberated RNA was captured on a second nucleic acid binding glass fiber filter membrane (Pall Corporation). An RNA wash buffer (Zymo Research (Orange, Calif.) was passed through the membrane to remove cellular debris while retaining RNA.

At this stage the following alternative methods may be applied:

(1) a vacuum is applied to the second membrane to dry and preserve the RNA for later elution and analysis, or (2) an elution buffer is passed through the second membrane and the eluate is collected in a storage tube.

Results:

As shown below in TABLE 3, the quality of RNA extracted using the Leukosorb® membrane after removal from the plastic housing, labeled as "WBC Capture" was compared to RNA that was extracted from a lysate that was captured on a silica membrane directly from the Leukosorb® membrane while still contained in the housing, labeled as "In-card WBC lysis." Also included in TABLE 3 below are three other commonly used methods of RNA isolation including E Lysis (Qiagen), Trizol purification and PAX gene (PreAnalytiX, Feldbackstrasse, Switzerland). The RNA quality was measured using the 28S/18S ratio using the Agilent 2100 Bioanalyzer (Agilent Technologies, Palo Alto, Calif.). It is known that the ~5 kilobase 28S rRNA is more susceptible to degradation than the ~2 kilobase 18S rRNA, so a higher 28S:18S rRNA value is associated with RNA that is more highly intact. As shown below, it was found that high quality RNA (e.g., RNA with a 28S118S ratio of at least 1.0 or greater), was captured and isolated in the presence of white blood cell lysate.

TABLE 3

| RNA Sample Source | Method of RNA Purification | 28s/18s |
| --- | --- | --- |
| Whole blood: Filter Pool 1 | WBC Capture | 1.6 |
| Whole blood: Filter Pool 2 | WBC Capture | 1.8 |
| Whole blood: Lysate Pool 1 | In-card WBC Lysis | 2.0 |
| Whole blood: Lysate Pool 2 | In-card WBC Lysis | 1.9 |
| Whole blood sample | E Lysis Protocol | ~1.0 |
| Whole blood sample | Trizol Protocol | ~1.0 |
| Whole blood sample | PAX gene Protocol | ~1.0 |

Conclusion:

The RNA purified using the in-card WBC lysis was found to be high quality, non-degraded RNA. The purification method was carried out in less than 15 minutes. Therefore, it is expected that an RNA isolation device containing a first white blood cell capture membrane and a second membrane which reversibly binds RNA would be capable of purifying high quality RNA from whole blood in less than 15 minutes, and may be done in less than 5 minutes, from the time of blood draw to RNA capture on the second membrane.

Example 4

This example describes the use of an alternative configuration of an RNA isolation device having a blood collection needle attached to the device.

Methods:

In one configuration, the RNA isolation device includes a septum through which a butterfly needle is inserted. The needle is inserted into a subject, 2-3 ml of blood are drawn through the needle directly into the device, and the blood is pulled through the Leukosorb® filter into a waste port. The blood is then processed in the same manner as described above in Example 3. In this alternative configuration, the first step to blood processing is accomplished without having to engage a control unit, thereby simplifying the instrument design, reducing the time between blood draw and RNA isolation, and providing a more efficient procedure for the phlebotomist.

Example 5

This Example describes an RNA isolation device including a reaction chamber and methods of use for RNA isolation and on-board RNA analysis.

Methods:

2 to 3 mL of whole blood from a patient is collected in a Vacutainer tube (Becton Dickinson, Franklin Lanes, N.J.). The blood sample is introduced into an RNA isolation device comprising a reaction chamber inserted into a control unit. The blood sample is processed as described above in Example 3 up to the step of RNA capture on the second nucleic acid binding glass fiber filter membrane. The RNA is then eluted in an elution buffer into a third sealed, thermal reaction chamber contained within the device. A 2.5 ml sample of whole blood will typically yield approximately 5 μg of total RNA. Once the RNA is eluted into the on-board reaction chamber, the following reactions are carried out.

RT-PCR Reaction:

The eluate comprising up to about 5 μg total RNA is introduced into the reaction chamber. A reaction mixture including 150 ng of random hexamers, 2 μl of 10×RT buffer, 4 μl of 25 mM $MgCl_2$, 2 μl of 0.1 M dithiothreitol, 1 μl RNase OUT, 1 μl of 50 U/μl SuperScript II and DEPC-treated water is introduced through a port in the reaction chamber from the reagent pack. The reaction chamber in the device is heated to a temperature of about 42° C. for a time sufficient (from 1 minute up to 1 hour) to create cDNA from the isolated RNA. The temperature of the reaction chamber is elevated by an external heating source, such as a Peltier device situated adjacent the reaction chamber which is controlled by feedback electronics on the control unit.

Conventional and Real-Time PCR:

Once the cDNA reaction is completed, sequence-specific DNA primers and a SYBR Green Master Mix (available from Applied Biosystems) are introduced via a port in the reaction chamber from the reagent pack. A protocol is selected using the control unit to perform a pre-set number of thermal profile cycles to amplify and label specific sequences for read-out for quantification relative to control amplification reactions run in parallel. Reactions of this type include Full Velocity QRT-PCR (Stratagene, San Diego), protocols, or such protocols as can be found in the literature (e.g., Wang and Seed, *Nucl. Acids Res.*, 31(24):e154; 1-8), that provide a read-out to quantify RNA levels.

An example of a suitable reaction profile is provided below:

The PCR mixture is pre-heated at 50° C. for 2 minutes and then at 95° C. for 10 minutes to activate the AmpliTaq Gold DNA polymerase, followed by 40 cycles of amplification (95° C. for 15 s; 60° C. for 30 s; 68° C. for 40 s). A final extension step is performed at 60° C. for 10 minutes. The fluorescence is then detected with a fluorescence signal detection unit associated with the control unit. Alternatively, the amplified material can be removed from the reaction chamber and further analyzed using standard techniques, such as microarrays.

Example 6

This Example describes a method of assigning an identifier to a blood sample and correlating the number to isolated RNA and optionally results obtained from the analysis of RNA isolated from the identified blood sample.

Method:

Referring to the system 100 as shown in FIGS. 7 and 8, the system 100 is prepared prior to use as follows. An operator installs a reagent pack 500 comprising the following reagents:

PBS Wash Buffer
Lysis Buffer
RNA Wash Buffer
Elution Buffer
Reverse Transcriptase Master Mix
PCR Master Mix A 2.5 to 3 mL blood sample is obtained from a subject and introduced into the disposable RNA isolation device 200, as described herein. The blood sample may be either preloaded into the first chamber 212 of the device prior to placement of the purification device onto the device interface of the processing instrument, or introduced into the device after placement onto the processing instrument. An optional step is to scan an identifier code associated with the device using a scanner on the control unit, and upload the identification code into a database in the system computer. The RNA purification proceeds as follows: the first waste valve 372 is opened, allowing a vacuum to draw the blood sample across the first WBC capture membrane 220 to the waste receptacle 600. The PBS wash buffer (from 100 µl to 1000 µl) is passed over the first WBC capture membrane 220 to remove non-WBC (e.g., erythrocytes, reticulocytes, platelets); and the PBS wash solution is ported to the waste receptacle 600. The first waste valve 372 is closed and the shutter valve 230 and second waste valve 374 are opened. The lysis buffer (from 100 µl to 1000 µl) is passed over the WBC capture membrane 220, producing a WBC lysate that is passed over the second RNA capture membrane 240. An optional step is the addition of RNA binding buffer (100 µl to 1000 µl along with the lysis buffer in order to improve RNA binding efficiency to the second membrane. While the second waste valve 374 remains in the open position, an RNA wash buffer (100 µl to 1000 µl) is passed over the second membrane 240 to remove cellular debris. An optional step is to also pass DNAse buffer (100 µl to 1000 µl) over the second membrane 240 to remove contaminating DNA prior to RNA elution. The captured RNA is then dried onto the second membrane under a vacuum. The purification device 200 containing purified RNA may then be processed according to one of the following methods:

Shipment of Device Containing RNA for Processing at a Remote Site

After the second membrane 240 in the device is dried under a vacuum, the device containing RNA 200 is removed from the control unit 300, packaged in a sealed container, and shipped to a remote location for processing. Upon removal of the device from the control unit, the control unit 300 sends a message to the processing facility identifying the device containing RNA and other desired information (e.g., device identifier, blood sample identifier, time, date, location, etc.). The RNA is then eluted and processed at the remote laboratory as described below.

Elution of the RNA from the Device and Analysis External to the Device

After the second membrane 240 in the device is dried under a vacuum, the second waste valve 374 is closed and an elution buffer is passed over the second membrane and collected in a RNase-free receptacle for analysis. The receptacle may also include an identifier number for tracking the RNA sample. The RNA sample may be analyzed or shipped to a remote laboratory. If the RNA sample is sent to a remote laboratory, upon elution of the RNA into the receptacle the control unit 300 sends a message to the processing facility identifying the receptacle containing the RNA and other desired information (e.g., device identifier, blood sample identifier, time, date, location, etc.).

Elution of the RNA into a Chamber in the Device and Analysis Internal to the Device After the second membrane 240 in the device is dried under a vacuum, the second waste valve 374 is closed and an elution buffer is passed over the second membrane and collected in a sealed reaction chamber housed in the device. The RNA is then analyzed by RT-PCR as follows:

10 µl to 100 µl of RT mix is added to the on-board chamber and the chamber is heated by a Peltier device associated with the control unit to a temperature of about 42° C. for a period of time from 1 minute to 1 hour. The reverse transcriptase enzyme is then inactivated by heating the chamber to a temperature from 70° C. to 95° C. for a time period ranging from 1 minute to 10 minutes. The reaction chamber is then cooled to 50° C. and 10 µl to 100 µl of PCR master mix with gene-specific primers are added from the reagent pack via a port in the chamber. The temperature of the chamber is then raised to about 95° C. for a time period from 1 minute to 10 minutes followed by repeated cycling through a temperature profile, such as 60° C. for 30 seconds, 72° C. for 30 seconds, 95° C. for 30 seconds. A reading is taken through an optical window in the reaction chamber using an optical detection system such as a fluorescent light source and a fluorescent reader until a signal is detected above a threshold value.

In an alternative configuration, a PCR master mix is used that contains more than one gene-specific primer and the optical detection system contains optical filters or laser diodes tuned to specific wavelengths are used that are able to detect more than one amplified species at a time.

After the data signal is detected and the read-out is complete, the computer associated with the control unit sends instructions to pass the results of the RNA analysis to a database that can be accessed by a physician or remotely to a centralized facility, where the results are utilized to determine a therapeutic course of action.

While the preferred embodiment of the invention has been illustrated and described, it will be appreciated that various changes can be made therein without departing from the scope of the invention.

The embodiments of the invention in which an exclusive property or privilege is claimed are as defined as follows:

1. A device for isolating RNA from a sample containing white blood cells, the device comprising:
   a device body that includes:
   an inlet port for receiving a sample containing white blood cells;
   a first chamber that includes a first membrane that binds white blood cells;
   a second chamber that includes a second membrane, wherein the second membrane is a glass-fiber filter that reversibly binds RNA;
   a valve fluidly coupling the first and second chambers;
   an outlet port for dispensing the isolated RNA;
   at least one reagent port for fluidly coupling at least one of the first and second chambers to at least one reagent reservoir, wherein the reagent port is not the same as the inlet port;
   at least one waste port for fluidly coupling at least one of the first and second chambers to a waste receptacle coupled to a vacuum source, wherein the waste port is not the same as an outlet port for isolated RNA; and wherein the inlet port is in fluid communication with the first chamber and the outlet port is in fluid communication with the second chamber.

2. The device of claim 1, wherein the first membrane selectively binds white blood cells.

3. The device of claim 1, wherein the sample containing white blood cells is whole blood.

4. The device of claim 1, wherein the device body further includes a waste receptacle in fluid communication with at least one of the first or second chamber.

5. The device of claim 1, wherein the inlet port is adapted to be removably attachable to a blood draw apparatus.

6. The device of claim 1, wherein the fluid flow between the at least one chamber, the at least one reagent receptacle, and the at least one waste receptacle is selectively controlled by a control unit.

7. The device of claim 6, wherein the valve fluidly coupling the first and second chambers is controlled by the control unit.

8. The device of claim 1, wherein the device body is in the shape of a card.

9. The device of claim 1, wherein the device is disposed of after a single use.

10. The device of claim 1, wherein the device comprises a use indicator.

11. The device of claim 10, wherein the use indicator is a unique identifier.

12. A device for isolating and analyzing RNA from a sample containing white blood cells, the device comprising:
a device body that includes:
an inlet port for receiving a sample containing white blood cells;
a first chamber that includes a first membrane that binds white blood cells;
a second chamber that includes a second membrane, wherein the second membrane is a glass-fiber filter that reversibly binds RNA;
a third thermal chamber, wherein the temperature of the third chamber is controlled by an external source;
a first valve fluidly coupling the first and second chambers;
at least one reagent port for fluidly coupling at least one of the first, second and third chamber to at least one reagent reservoir, wherein the reagent port is not the same as the inlet port; and
at least one waste port for fluidly coupling the at least one of the first, second and third chamber to a waste receptacle coupled to a vacuum source, wherein the waste port is not connected to the first valve fluidly coupling the first and second chambers.

13. The device of claim 12, wherein the first membrane selectively binds white blood cells.

14. The device of claim 12, wherein the sample containing white blood cells is whole blood.

15. The device of claim 12, wherein the device body further includes a waste receptacle in fluid communication with at least one of the first or second chambers.

16. The device of claim 12, wherein the inlet port is adapted to be removably attachable to a blood draw apparatus.

17. The device of claim 12, wherein the fluid flow between the at least one chamber, the at least one reagent receptacle, and the at least one waste receptacle is selectively controlled by a control unit.

18. The device of claim 17, wherein the first valve fluidly coupling the first and second chambers is controlled by the control unit.

19. The device of claim 12, wherein the device body further includes a detection window downstream of the second chamber adapted to allow a detector external to the device body to detect at least one characteristic of the isolated RNA.

20. The device of claim 12, wherein the device body is in the shape of a card.

21. The device of claim 12, wherein the device is disposed of after a single use.

22. A system for isolating RNA from a sample containing white blood cells, the system comprising:
a device body that includes:
an inlet port for receiving a sample containing white blood cells;
a first chamber that includes a first membrane that binds white blood cells;
a second chamber that includes a second membrane, wherein the second membrane is a glass-fiber filter that reversibly binds RNA;
a valve fluidly coupling the first and second chambers;
an outlet port for dispensing the isolated RNA;
at least one reagent port for fluidly coupling at least one of the first and second chambers to at least one reagent reservoir, wherein the reagent port is not the same as the inlet port; and
at least one waste port for fluidly coupling at least one of the first and second chambers to a waste receptacle coupled to a vacuum source, wherein the waste port is not the same as an outlet port;
a control unit comprising a manifold for fluidly coupling the at least one chamber to the at least one reagent reservoir and to the at least one waste receptacle, the control unit controlling the fluid flow on the device; and
a reagent reservoir comprising at least one reagent for isolating RNA, the reservoir removably attached to the control unit.

23. The system of claim 22, wherein the first membrane selectively binds white blood cells.

24. The system of claim 22, wherein the reagent reservoir includes a lysis buffer comprising Tris-buffered, guanidine thiocyanate and beta-mercaptoethanol.

25. The system of claim 22, wherein the RNA is bound to the second membrane within 15 minutes from introduction of the sample into the device.

26. The system of claim 22, wherein the device body further includes a third thermal chamber, wherein the temperature of the third chamber is controlled by the control unit.

27. The system of claim 22, wherein the isolated RNA has a 28S/18S RNA ratio of greater than 0.8.

28. A method of isolating RNA from whole blood, comprising:
introducing a sample of whole blood into an inlet of a device, wherein the blood sample is introduced into the device from a subject through a blood draw apparatus that is attached to the inlet of the device;
capturing the white blood cells on a first membrane in the device, wherein the first membrane binds white blood cells and does not substantially bind red blood cells;
washing the first membrane comprising captured white blood cells with a first wash buffer to remove the red blood cells;
lysing the captured white blood cells with a lysis buffer to produce a lysate comprising white blood cell RNA;
capturing the white blood cell RNA in the lysate on a second membrane in the device; wherein the second membrane is a glass-fiber filter that reversibly binds the white blood cell RNA in the presence of the lysis buffer;
washing the second membrane with a second wash buffer to remove the lysis buffer; and drying the second membrane, wherein purified RNA from the white blood cells is reversibly bound to the second membrane in the device and is substantially free of hemoglobin RNA.

29. The method of claim 28, further comprising eluting the RNA bound to the second membrane with an elution buffer.

30. The method of claim 28, wherein the device including RNA bound to the second membrane is stored prior to elution.

31. The method of claim 28, wherein the device including RNA bound to the second membrane is shipped to a different location prior to elution.

32. The method of claim 28, wherein the lysis buffer comprises Tris-buffered, guanidine thiocyanate and beta-mercaptoethanol.

33. The method of claim 29, wherein the elution buffer is RNase-free water.

34. The method of claim 28 wherein the purified RNA has a 28S/18S RNA ratio of greater than 0.8.

35. A system for isolating and tracking RNA from a sample containing white blood cells, the system comprising:
   a disposable RNA isolation device having a device body that includes a first membrane in a first chamber that binds white blood cells and a second membrane in a second chamber, wherein the second membrane is a glass-fiber filter that reversibly binds RNA, an inlet port for receiving a the sample containing white blood cells, a valve fluidly coupling the first and second chambers, at least one reagent port for fluidly coupling at least one of the first and second chambers to at least one reagent reservoir, wherein the reagent port is not the same as the inlet port; at least one waste port for fluidly coupling at least one of the first and second chambers to a waste receptacle coupled to a vacuum source, wherein the waste port is not connected to the valve fluidly coupling the first and second chambers;
   an identifier uniquely associated with the disposable RNA isolation device;
   a control unit comprising a memory and device interface for controlling fluid movement in the disposable RNA isolation device, wherein the RNA isolation device is removably attachable to a portion of the control unit; and
   an identifier recording device capable of detecting and transmitting the device identifier into the memory of the control unit;
   wherein the control unit is accessed remotely on a network.

36. The system of claim 35, wherein the RNA isolation device further comprises a thermal chamber.

37. The system of claim 36, wherein the system further comprises means for detecting at least one characteristic of RNA isolated in the RNA isolation device.

38. The system of claim 37, wherein the at least one characteristic of RNA is stored in the memory of the control unit.

39. The device of claim 1, wherein the device is a self-contained closed device for minimizing risk of exposure to blood-borne pathogens that may be present in the blood sample under analysis.

* * * * *